United States Patent
Bijno et al.

(10) Patent No.: US 10,583,120 B2
(45) Date of Patent: Mar. 10, 2020

(54) COMPOSITION HAVING A MUSCLE-RELAXANT AND ANTI-INFLAMMATORY ACTIVITY

(71) Applicant: Kolinpharma S.p.A., Milan (IT)

(72) Inventors: Domenico Bijno, Milan (IT); Carmine Di Vincenzo, Milan (IT); Emanuele Lusenti, Milan (IT); Alberto Martina, Milan (IT); Ritapaola Petrelli, Milan (IT)

(73) Assignee: Kolinpharma S.p.A., Milan (IT)

( * ) Notice: Subject to any disclaimer, the term of this patent is extended or adjusted under 35 U.S.C. 154(b) by 0 days.

(21) Appl. No.: 15/503,082

(22) PCT Filed: Aug. 18, 2015

(86) PCT No.: PCT/IB2015/056268
§ 371 (c)(1),
(2) Date: Feb. 10, 2017

(87) PCT Pub. No.: WO2016/027225
PCT Pub. Date: Feb. 25, 2016

(65) Prior Publication Data
US 2017/0224659 A1    Aug. 10, 2017

(30) Foreign Application Priority Data

Aug. 19, 2014 (IT) .............. TO2014A0672

(51) Int. Cl.
| | | |
|---|---|---|
| *A61K 31/405* | (2006.01) | |
| *A61K 33/06* | (2006.01) | |
| *A61K 36/324* | (2006.01) | |
| *A61K 31/19* | (2006.01) | |
| *A61K 9/00* | (2006.01) | |
| *A61K 31/56* | (2006.01) | |

(52) U.S. Cl.
CPC .......... *A61K 31/405* (2013.01); *A61K 9/0053* (2013.01); *A61K 31/19* (2013.01); *A61K 31/56* (2013.01); *A61K 33/06* (2013.01); *A61K 36/324* (2013.01)

(58) Field of Classification Search
None
See application file for complete search history.

(56) References Cited

U.S. PATENT DOCUMENTS

| | | | | |
|---|---|---|---|---|
| 5,922,765 A | * | 7/1999 | Fleming ............... | A61K 9/0019 514/557 |
| 2010/0226968 A1 | | 9/2010 | Holgate | |
| 2011/0159048 A1 | | 6/2011 | Crain et al. | |
| 2011/0159120 A1 | * | 6/2011 | Gokaraju ............ | A61K 36/324 424/725 |
| 2014/0161955 A1 | * | 6/2014 | Wadhwa ................ | A23L 33/16 426/590 |

OTHER PUBLICATIONS

Ammon, "Modulation of the immune system by Boswellia serrata extracts and boswellic acids", Phytomedicine, 2010, vol. 17, pp. 862-867.
Cheng et al., "Control of cyclooxygenase-2 expression and tumorigenesis by endogenous 5-methoxytryptophan", PNAS, 2012, vol. 109, No. 33, pp. 13231-13236.
Madan et al., "Anti-inflammatory activity of L-tryptophan and DL-tryptophan", The Indian Journal of Medical Research, 1978, vol. 68, pp. 708-713.
Manabe et al., "Characterization of an Acute Muscle Contraction Model Using Cultured C2C12 Myotubes", PLOS One, 2012, vol. 7, Issue 12, p. e52592.
Mouithys-Mickalad et al., "Effects of COX-2 inhibitors on ROS produced by Chlamydia pneumoniae-primed human promonocytic cells (THP-1)", Biochemical and Biophysical Research Communications, 2004, vol. 325, pp. 1122-1130.
Puchert et al., "Slowing effect of $Mg^{2+}$ on contractile kinetics of skinned preparations of rat hearts depending on myosin heavy chain isoform content", Pflugers Arch—Eur J Physiol, 2003, vol. 447, pp. 135-141.
Sharma et al., "Magnesium sulfate suppreses L-Type calcium currents on the basilar artery smooth muscle cells in rabbits", Neurological Research, 2012, vol. 34, No. 3, pp. 291-296.
Shi et al., "Mechanism of magnesium activation of calcium-activated potassium channels", Nature, 2002, vol. 418, pp. 876-880.
Siddiqui, "Boswellia Serrata, A Potential Antiinflammatory Agent: An Overview", Indian Journal of Pharmaceutical Sciences, 2011, vol. 73, No. 3, pp. 255-261.
Su et al., "Phosphoinositide 3-kinase/Akt pathway is involved in mediating the anti-inflammation effects of magnesium sulfate", Journal of Surgical Research, 2013, vol. 185, pp. 726-732.
Suzuki-Kakisaka et al., "Magnesium Sulfate Increases Intracellular Magnesium Reducing Inflammatory Cytokine Release in Neonates", American Journal of Reproductive Immunology, 2013, vol. 70, pp. 213-220.
Tica et al., "Magnesium ion inhibits spontaneous and induced contractions of isolated uterine muscle", Gynecological Endocrinology, 2007, vol. 23, No. 7, pp. 368-372.
International Search Report and Written Opinion, Application No. PCT/IB2015/056268, dated Nov. 17, 2015.
EP Search Report, Application No. 15774695.9, dated Nov. 22, 2018.
Cohen et al., "The Pharmacologic Treatment of Muscle Pain", American Society of Anesthesiologists, Inc., vol. 101, No. 2, 2004, pp. 495-526.
Nuan-Yen et al., "Phosphoinositide 3-kinase/Akt pathway is involved in mediating the ant-inflammation effects of magnesium sulfate", Journal of Surgical Research, vol. 185, 2013, pp. 726-732.
Supakatisant et al., "Oral magnesium for relief in pregnancy-induced leg cramps: a randomised controlled trial", Maternal & Child Nutrition, vol. 11, 2015, pp. 139-145.

* cited by examiner

*Primary Examiner* — Bong-Sook Baek
(74) *Attorney, Agent, or Firm* — MacMillan, Sobanski & Todd, LLC

(57) ABSTRACT

A pharmaceutical composition or dietary supplement having a muscle-relaxant and anti-inflammatory activity is described, which is effective in the treatment of muscle, bone, articular and tendon pathologies, comprising, as active ingredients, a combination of magnesium, at least one ketoboswellic acid and L-tryptophan.

5 Claims, 6 Drawing Sheets

COMPOSITION HAVING A MUSCLE-RELAXANT AND ANTI-INFLAMMATORY ACTIVITY

This is a national stage application filed under 35 U.S.C. § 371 of international application PCT/IB2015/056268, filed under the authority of the Patent Cooperation Treaty on Aug. 18, 2015, published; which claims the benefit of Patent Application No. TO2014A000672, filed on Aug. 19, 2014. The entire disclosures of all the aforementioned applications are expressly incorporated herein by reference for all purposes.

The invention relates to a composition having a muscle-relaxant and anti-inflammatory activity, for use as a dietary supplement or medicament in the treatment of muscle, bone, articular or tendon pathologies.

The subject of the invention is a formulation for oral administration, which is free of particular contraindications both as regards the individuals to whom it may be administered and as regards the administered amount, and which has an anti-inflammatory and muscle-relaxant effect.

The composition that is the subject of the present invention is characterized in that it comprises, as active ingredients, a combination of magnesium, L-tryptophan and at least one ketoboswellic acid, for instance 3-acetyl-11-keto-β-boswellic acid (AKBA).

Magnesium is a mineral involved in various biochemical reactions and plays a crucial role in the production and use of energy. It is considered to be of valuable assistance as regards the muscular system (cofactor necessary for ensuring muscle elasticity and physiological sliding of the myofibrils) and the nervous system (key role in nerve conduction as it is an active element in many types of channels that ensure physiological transmission of the action potential in the case of functionality of the tissue). It is precisely because of its involvement in so many biological activities that deficiencies in this mineral are related to stress, anxiety, insomnia, muscle stiffness and nocturnal or recurrent cramp.

Magnesium is involved both in the process of contraction and in the process of transmission of the nerve impulse to the neuromuscular plate.

Every striated muscle is formed from a set of parallel filaments, increasingly smaller, nested within one another. To understand where magnesium is incorporated, the contractile unit is briefly described. Muscle fibres (individual cells) consist of myofibrils; each of them is formed from thousands of sarcomeres (contractile units), each delimited by two ends of the Z line. Sarcomeres in turn consist of thick filaments of myosin molecules and thin actin filaments. A muscle contracts when the thin filaments slide along the myosin filaments, leading to shortening of the sarcomere. This movement is determined by the attachment of the myosin heads to specific sites on the actin filaments which, by means of an arching movement, brings about contraction of the fibre. The movement may take place by means of the energy supplied by the ATP molecules and the intervention of $Ca^{2+}$ ions. ATP bonds to the myosin head (each myosin filament bears about 350 heads) which is initially in a low-energy configuration. By means of the cleavage of ATP to ADP and a phosphate group, the myosin, adopting a high-energy conformation, obtains the energy supply required for the head to be able to move. The cleavage of ATP takes place by means of other motor proteins, kinesins, which have ATPase activity. To develop this activity, they require the presence of magnesium as cofactor. Without the necessary energy, myosin cannot attack actin within physiological timeframes causing muscle contraction, from which mechanism the decontracting activity of magnesium may be deduced.

However, magnesium does not only regulate the activity of the kinesins mentioned above, but of all enzymes with ATPase activity, therefore also the calcium-ATPases; magnesium thus indirectly regulates the cytoplasmic calcium concentration, which is interesting activity since calcium is an essential element both for contraction (sarcoplasmatic calcium) and for nerve conduction and for maintaining the membrane potential and ensuring correct impulse transmission.

As regards impulse transmission, magnesium is a central player also in regulating the NMDA receptors (representing one of the three types of ionotropic glutamate receptors, which are so named because of the selective N-methyl-D-aspartate ligand). These are post-synaptic receptors, which are physiologically slower than the AMPA and KA receptors (the other two types) and are highly permeable to calcium. Opening of the channel requires the attainment of a particular action potential, which may be reached by means of the presence of magnesium, which blocks the channel until the threshold is reached. Early opening of the channel would result in the signal being compromised. Consequently, magnesium is responsible for maintaining the physiological functions of the nervous system.

Another fundamental process in which magnesium is involved is the phosphorylation of glucose to glucose 6-phosphate in the first step of glycolysis. Specifically, the mineral is a cofactor of the hexokinase enzyme, which is responsible for the phosphorylation. This reaction is essential for starting the glycolysis cycle and thus for enabling the cell to produce the energy required to sustain normal biological functions. When magnesium is deficient, a general metabolic slowing-down takes place, caused by the low production of energy, and as such it is important to consider magnesium for cellular energy refueling.

According to a preferred embodiment, magnesium is present in the composition of the invention in the form of magnesium bisglycinate.

The composition that is the subject of the present invention also comprises the dry extract of *Boswellia serrata*. *Boswellia serrata* is characterized by the presence, in the plant complex, of numerous bioactive substances, such as ketoboswellic acids. The latter are reported in the literature for their anti-inflammatory, immunomodulatory, antitumoral and antiasthmatic activities. According to a preferred embodiment, the dry extract of *Boswellia serrata* is an extract rich in 11-keto-β-boswellic acids (AKBA), which have higher anti-inflammatory activity.

The composition that is the subject of the present invention is intended for muscle distension in the case of contracture, but it is known that situations of muscle stiffness, cramp and tension are related to a general stress of the area concerned, which, symptomatically, is perceived as pain. In reality, this is a consequence of the inflammation that becomes established in the muscles and nerves of the area concerned. For this reason, anti-inflammatory activity is also important, which makes it possible to re-establish the functionality in a shorter time relative to an action solely directed towards muscle relaxation. This anti-inflammatory activity is provided by *Boswellia serrata*, which develops both direct action on inhibiting the leukocytic elastases produced by the leukocytes, performed by the AKBAs contained therein, and an action on inhibiting the 5 lipoxygenases, with a consequent reduction thereof in the inflammation mediators downstream.

The composition that is the subject of the present invention also has the advantage of not only acting on the symptomatology relating to contracture, but of also acting by modulating the tone of the mood and raising the pain threshold of the patient. This activity is developed in particular by its third component, L-tryptophan, which is a known precursor of serotonin and melatonin, which are responsible for the tone of the mood (serotonin directly and melatonin indirectly by improving the sleep cycle).

Further characteristics of the composition of the invention and of its use are defined in the attached claims, which form an integral part of the present description.

The combination of the abovementioned active ingredients in the composition according to the invention is particularly advantageous since they develop a synergistic effect, both as regards the muscle-relaxant action and as regards the anti-inflammatory action.

The compositions of the invention may be formulated in any form suitable for oral administration, for example as soft or hard gelatin capsules, tablets, effervescent or chewable tablets, granules or powders in a sachet, controlled-release solid form, chewing gum and the like.

The compositions of the present invention may be formulated in a manner suitable for oral administration and will be prepared according to conventional methods that are well known in the pharmaceutical field, such as those described in "Remington's Pharmaceutical Handbook", Mack Publishing Co., N.Y., USA, using excipients, diluents, fillers and anticaking agents that are acceptable for the final use thereof.

The experimental section that follows describes studies that were performed relating to the biological effects of the composition of the invention. In the description of the studies performed, reference is made to the attached figures, in which.

Figure 1:
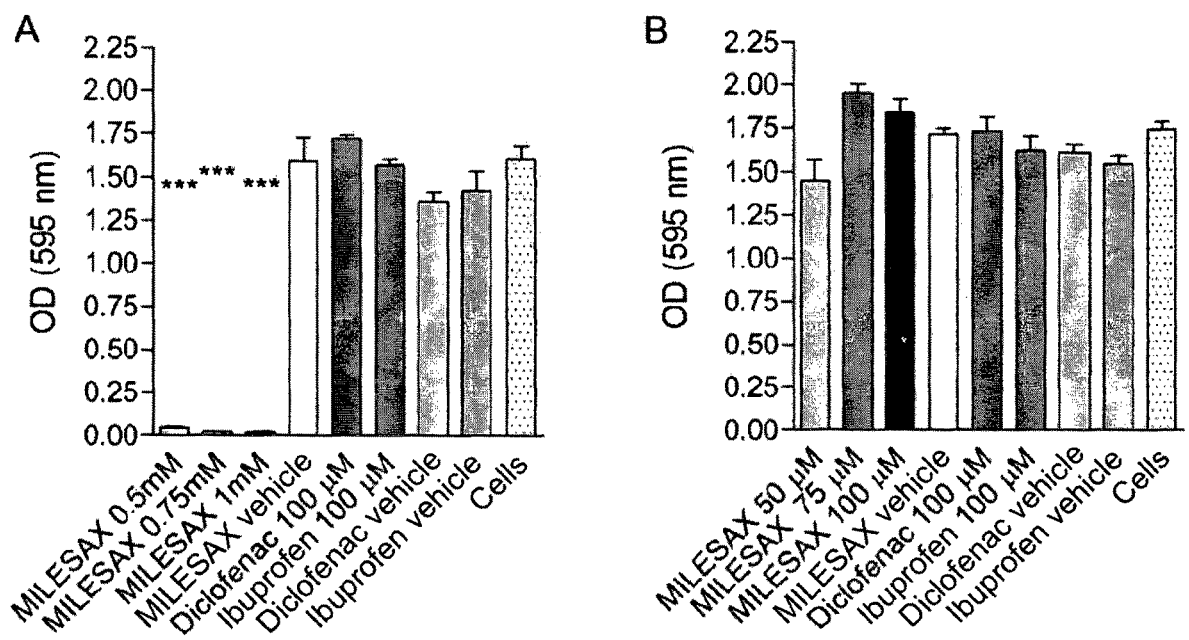
FIG. 1 shows the results of the MTT test on THP-1 cells incubated with Milesax; the absorbance at 595 nm was measured in the various wells incubated for 16 hours with the indicated compounds at the indicated concentrations; each bar represents the average of at least 4 different wells (***$p<0.001$ relative to the vehicle Milesax)

A particularly preferred formulation of the composition of the invention, used in the experimental studies, is also given hereinbelow. In addition to the indicated active ingredients, the formulation comprises suitable excipients and optionally flavourings and colorants.

FORMULATION EXAMPLE 4.5 g SACHET

| | |
|---|---|
| Magnesium | 225 mg |
| *Boswellia serrata* extr. | 175 mg |
| of which AKBA | 52.5 mg |
| L-Tryptophan | 150 mg |

The recommended dose is one or two sachets per day.

EXPERIMENTAL SECTION

Rationale

The composition described above in the formulation example, referred to hereinabove as MILESAX, was used in the experimental study illustrated in the present description.

Extracts from the gum resin of *Boswellia serrata* and certain components thereof such as boswellic acids (BAs) may influence the immune system in various ways. For example, BAs may interact with the production and release of cytokines. It has been reported that BAs inhibit activation of the transcription factor NF-kB giving rise to a reduction in TNFα and various other cytokines, such as the interleukins IL-1β, IL-2, IL-4, IL-6 (Ammon H. P., 2010, Phytomedicine, 17(11): 862-7). In a similar manner to BAs, an endogenous tryptophan metabolite (5-methoxytryptophan) may also have anti-inflammatory action, regulating the expression of cyclooxygenase-2 (COX-2), the enzyme responsible for the synthesis of prostaglandins following inflammatory stimuli (Cheng H. H. et al., 2012, PNAS 109(33): 13231-6). It is also known that magnesium may have muscle-relaxant effects mediated by inhibition of the type-L calcium channels in smooth muscle cells of rabbit arteries (Sharma N. et al., 2012, Neurol. Res. 34(3): 291-6), and as such it is capable of reducing spontaneous contractions and contractions induced by oxytocin in muscle cells derived from the endometrium (Tica V. I. et al., 2007, Gynecol. Endocrinol. 23(7): 368-72). Magnesium is also known as an activator of the calcium-activated potassium channels, which are essential for modulating muscle contraction and neuronal activity (Shi J. et al., 2002, Nature 418: 876-880) and variations in magnesium concentration may modulate the contractility of cardiac muscle (Puchert E. et al., 2003, Pflugers Arch. 447(2): 135-41).

Object Of The Study

In the present experimental study, the anti-inflammatory activity of MILESAX in human monocyte cell cultures (THP-1 cells) following stimulation with LPS (lipopolysaccharide, one of the components of the outer membrane of Gram-negative bacteria), was analysed. The capacity of MILESAX to inhibit transduction of the signal which, from the extracellular stimulus (LPS), leads to the production of the cytokines TNF-α, IL-1β and IL-6 was evaluated quantitatively by means of an Elisa test (Test 1).

The muscle-relaxant activity of MILESAX in primary cell cultures of human skeletal muscle was also analysed, as was the capacity of the compound to modulate the contractile activity of differentiated myotubes in culture following stimulation with carbacol, a non-hydrolysable analogue of acetylcholine (neurotransmitter of the neuromuscular synapse).

Materials and Methods

Milesax

Since the individual components of MILESAX do not have the same solubility characteristics, they were each dissolved in the appropriate solvent and then mixed in the identical proportions of MILESAX to reconstitute the whole compound, as illustrated in Table 1 below.

TABLE 1

| Component | [final] in mM | solvent |
|---|---|---|
| Magnesium | 1.0 | Medium |
| B. serrata | 0.3 | DMSO |
| L-tryptophan | 0.6 | $H_2O$ |

The concentration of magnesium 1 mM was taken as reference (Suzuki-Kakisaka et al., American Journal of Reproductive Immunology 70 (2013) 213-220).

The positive controls with which were compared the effects produced by MILESAX in the various tests were: diclofenac and ibuprofen for the anti-inflammatory effect (Test 1), eperisone hydrochloride and thiocolchicoside for the muscle-relaxant effect (Test 2).

Cells

Human THP-1 cells derived from acute monocytic leukaemia (ATCC, cat. N. TIB-202) were cultured in RPMI-1640 medium (LifeTechnologies, cat. N. 21870-076) with the addition of sodium pyruvate 1 mM, HEPES 10 mM, L-glutamine 2 mM, 2-mercaptoethanol 0.05 mM, and foetal bovine serum to a final concentration of 10%. The cells were maintained in an incubator at 37° C. and 5% $CO_2$ and seeded every 3-4 days at a density of about $5 \times 10^5$ cells/ml.

For all the following tests, the cells were seeded in the evening in 96-well multi-well plates and incubated with various concentrations of MILESAX, of its vehicle, of the positive control(s) in whole medium.

After about 16 hours of incubation, the cells were differentiated in serum-free medium for 2 hours in the presence or absence of LPS (1 µg/ml).

The human skeletal muscle cells (Clonetics™ Skeletal Muscle Myoblast Cell Systems, Lonza) were cultured in Skeletal Muscle Growth Media-2 (CC-3244, Lonza) containing hEGF (human Epidermal Growth Factor), dexamethasone, L-glutamine, foetal bovine serum and gentamicin/amphotericin B. The cells were maintained in an incubator at 37° C. and 5% $CO_2$ and seeded every 3-4 days at a density of about 3500 cells/cm², the medium being exchanged with fresh medium daily. The myoblasts were differentiated into myotubes in differentiation medium (DMEM: F12, with the addition of 2% of horse serum). The differentiated myotubes were used for the experiments from the fourth to the seventh day of maintenance in differentiation medium.

MTT Test (Test 0)

To check that the incubation with MILESAX at the concentrations and for the times chosen was not toxic to the cells, one or more MTT tests (Test 0) were performed. This colorimetric test is based on the transformation of the tetrazolium salt MTT (yellow) into formazan (violet), by the succinate-tetrazolium reductase system, which belongs to the mitochondrial respiratory chain and is active only in metabolically active cells. Briefly, the cells grown in a 96-well multi-well plate were incubated with MTT solution for 4 hours.

An insoluble colorant forms during this period, which, after dissolving by adding dissolution solution to the samples (10% SDS in 10 mM HCl) and after incubating overnight in an incubator, may be quantified by reading the absorbance of the samples at 595 nm (using 750 nm as reference wavelength). The absorbance measured correlates directly with the number of live cells.

Elisa Test (Test 1)

The anti-inflammatory effect of MILESAX was studied via an ELISA test (Enzyme-Linked Immunosorbent Assay, Biolegend, Inc.), by quantifying the production of pro-inflammatory cytokines in the culture medium following treatment with MILESAX and with various controls.

In the "sandwich" ELISA test, a 96-well plate is covered with a monoclonal antibody specific for a given cytokine. The standards and samples are added to the wells and the cytokine of interest bonds the uptake antibody immobilized to the bottom of the well. Next, an anti-cytokine biotinylated antibody is added to the wells so that an antibody-antigen-antibody "sandwich" is formed. Horseradish peroxidase combined with streptavidin is then added, followed by a solution of tetramethylbenzidene (TMB), which, by reacting with the peroxide, produces a blue-coloured compound, the intensity of which colour is proportional to the amount of cytokine present. The addition of a sulfuric acid solution changes the colour of the solution from blue to yellow, blocking the development of the colour and allowing accurate reading of the absorbance of the samples at 450 nm.

The cells incubated with the various overnight treatments were then differentiated for 2 hours in serum-free medium and simultaneously stimulated with LPS (lipopolysaccharide, one of the components of the outer membrane of Gram-negative bacteria). At the end of the treatment, the supernatant was collected and stored at −80° C. until the time of use for the test. The cells were used to measure the total protein content in the various samples. The concentrations of cytokines released into the culture medium were then expressed as pg of cytokine/mg of total protein of the sample. In this way, any differences in cytokine concentration in the medium due to a different amount of cells in the samples were eliminated.

Evaluation of the Muscle-relaxant Effect (Test 2)

For the evaluation of the muscle-relaxant effect of MILESAX, human myoblasts were seeded onto microscope slides and, once they had reached at least about 70% confluence, they were maintained in differentiation medium for 4-7 days before being used for the experiments. The contractile activity of the myotubes was recorded with a TCS SP5 confocal microscope (Leica Microsystems) in transmitted-light mode with the 40× objective lens (HCX PL APO, 1.25 NA, Leica Microsystems) using the incubator associated with the microscope to maintain the cells under a controlled atmosphere (37° C., 5% $CO_2$).

The myotubes were stimulated with 3 mM of carbacol, dissolved in differentiation medium, for at least 20 minutes before starting the recordings and maintained in differentiation medium containing carbacol and the various treatments throughout the experiments.

Statistical Analysis

The quantitative data relating to the various tests were expressed as the mean±standard error. The one-way ANOVA statistical test (comparison between more than two groups) or the unpaired T test (comparison between two groups) were used to reveal statistically significant differences between the various samples.

Results

Identification Doses and Treatment Times (Test 0)

The THP-1 cells were incubated overnight with successive dilutions of MILESAX, starting from the composition having as reference a magnesium concentration of 1 mM. To exclude a possible toxic effect attributable to the chosen incubation protocol, the cell vitality was quantified by means of an MTT test. The data obtained in two different experimental days are collated in FIG. 1. Since the first tested concentrations of MILESAX (0.5, 0.75 and 1 mM) showed high cell mortality, the following tests were performed with MILESAX 50, 75 and 100 µM. At these concentrations of compound, the measured absorbance is not statistically different from that of the control (cells incubated with the MILESAX vehicle referred to the highest concentration).

In the same manner, incubation with the positive controls diclofenac and ibuprofen at a concentration of 100 µM (Mouuthys-Mickalad A. et al., BBRC, 2004, vol. 325, pages 1122-30) showed no toxic effect on the cells. The concentrations of the individual components in the three dilutions of MILESAX used in the following tests are given below, in Table 2:

TABLE 2

Concentration of the individual components of MILESAX in the three dilutions used for tests 1 and 2.

| Component | [final] in mM | [final] in mM | [final] in mM |
|---|---|---|---|
| Magnesium (from magnesium bisglycinate) | 0.1 | 0.075 | 0.05 |
| Boswellia serrata | 0.03 | 0.0225 | 0.015 |
| L-Tryptophan | 0.06 | 0.045 | 0.03 |

Anti-Inflammatory Activity in a Human Monocyte Cell Line (Test 1)

The anti-inflammatory activity of MILESAX was studied by quantifying the inhibition of production of pro-inflammatory cytokines by means of an ELISA test (Test 1).

Figure 2:
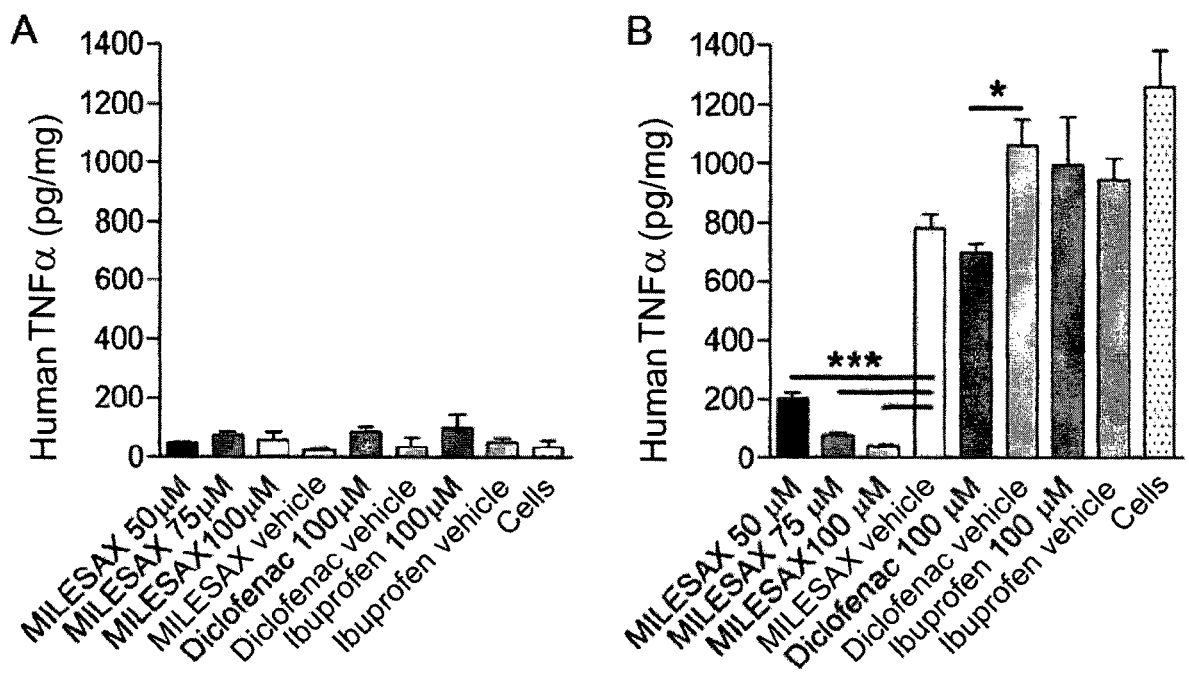
FIG. 2 shows the results of the quantification of TNFα in the culture medium of differentiated THP-1 monocytes after pre-incubation with MILESAX and the various controls in the absence of an inflammatory stimulus (A) or following stimulation with LPS 1 µg/ml for 2 hours (B). (***=$p<0.001$;*=$p<0.05$)

Release into the culture medium of the pro-inflammatory cytokines TNFα, IL-1β and IL-6 from the differentiated THP-1 monocytes was evaluated both in the absence and in the presence of stimulation with LPS for 2 hours. The data obtained for TNFα are collated in FIG. 2.

In the absence of inflammatory stimulus, the production of TNFα was very low, but, as expected, was appreciably amplified by stimulation with LPS.

Incubation for 16 hours with MILESAX at all the tested concentrations (50, 75 and 100 µM) led to a statistically significant reduction in the release of TNFα relative to the control condition (incubation with the MILESAX vehicle, white bar). The release of TNFα into the culture medium following incubation with the three concentrations of MILESAX was significantly smaller compared with the positive controls diclofenac and ibuprofen (p<0.001, one-way ANOVA test). While incubation with diclofenac 100 µM significantly reduced the release of TNFα relative to incubation solely with diclofenac vehicle (p<0.05, T test), incubation with ibuprofen 100 µM did not lead to any reduction in the release of TNFα relative to the control.

Figure 3:
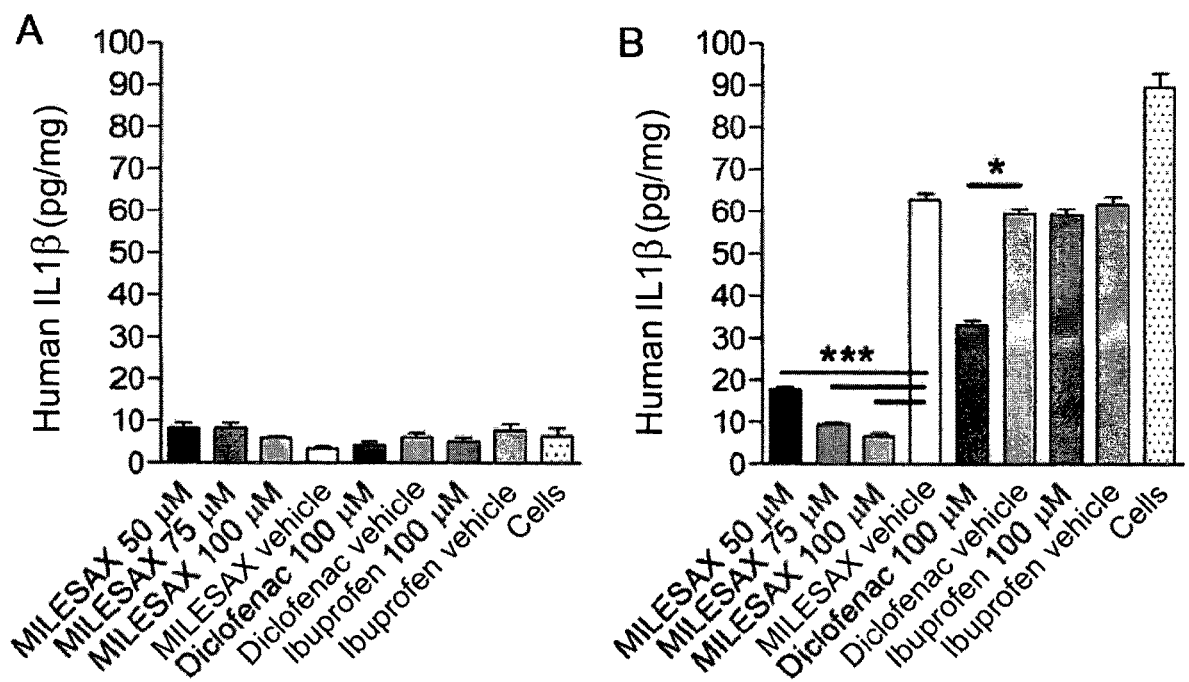
FIG. 3 shows the results of the quantification of IL-1β in the culture medium of differentiated THP-1 monocytes after pre-incubation with MILESAX and the various controls in the absence of an inflammatory stimulus (A) or following stimulation with LPS 1 µg/ml for 2 hours (B). (***=$p<0.001$;*=$p<0.05$)

The data relating to the quantification of IL-1β are collated in FIG. 3. As for TNFα, the quantification of IL-1β also showed a significant increase in the release following inflammatory stimulus with LPS, although smaller than the increase measured for TNFα. In this case also, the reduction in IL-1β release was statistically significant relative to the control at all the MILESAX tested concentrations and similar to or better than that for diclofenac, which was, nevertheless, effective in reducing the release of IL-1β. Ibuprofen, in contrast, had no effect on the release of IL-1β.

Figure 4:
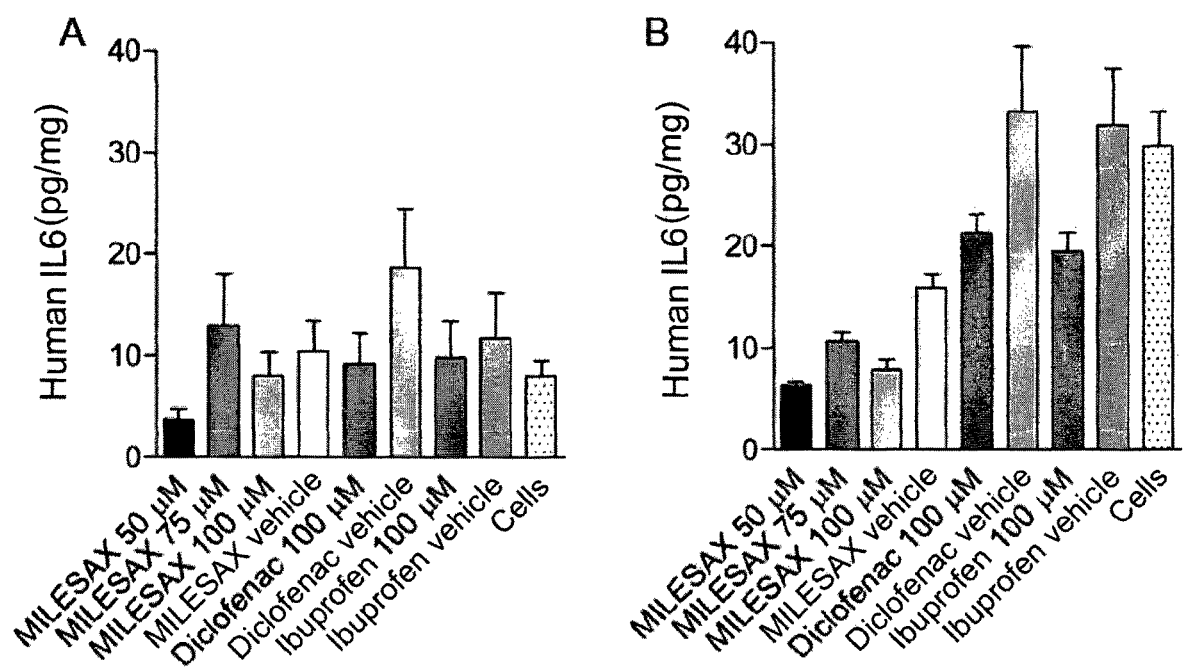
FIG. 4 shows the results of the quantification of IL-6 in the culture medium of differentiated THP-1 monocytes after pre-incubation with MILESAX and the various controls in the absence of an inflammatory stimulus (A) or following stimulation with LPS 1 µg/ml for 2 hours (B)

The data relating to the quantification of IL-6 are collated in FIG. 4. The release of IL-6 was not significantly stimulated by stimulation with LPS, probably requiring longer incubation times. Although a tendency of the compounds to reduce the production of cytokines by the monocytes was observed, no effect was statistically significant, except for the comparison between the three MILESAX concentrations and the cells alone (p<0.001 for MILESAX 50 µM and p<0.01 for MILESAX 75 and 100 µM).

Evaluation of the Muscle-Relaxant Effect (Test 2)

Human muscle myoblasts in culture are capable of differentiating into multinuclear myotubes that are capable of contracting following electrical stimuli or exposure to acetylcholine receptor agonists.

Not all the myotubes in the culture were capable of contracting, and similarly it was never possible to observe spontaneous contractions only in differentiation medium. For this reason, the differentiated myotubes were stimulated with carbacol 3 mM in differentiation medium. The contractile activity of the identified active cell(s) was recorded with a confocal microscope in transmitted light, with an image acquired every 151 ms. After the first 5 minutes of controlling the activity of the myotube in differentiation medium, the same cell was exposed to the various treatments, MILESAX or thiocolchicoside (Muscoril) and washing (wash, exposure once again to differentiation medium). Carbacol was present throughout the recordings.

Modulation of the contractile activity of the myotubes was quantified by analysing two parameters: the number of contractions per minute and the mean displacement of the myotube during the contractile activity (Manabe Y. et al., 2012, PLOS ONE 7(12): 1-10).

Figure 5:
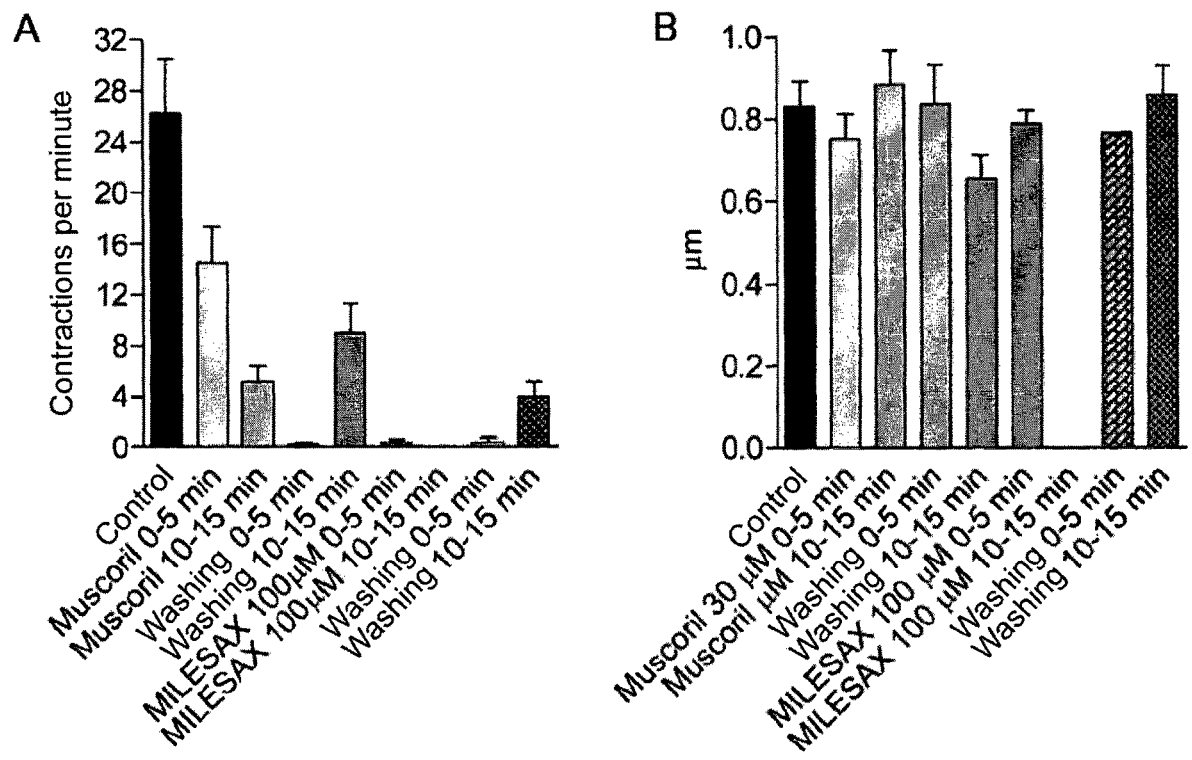
FIG. 5 shows the results of the quantification of the contractions per minute (A) and of the average displacement of the myotube calculated as the distance traveled during a single contraction taken at an easily identifiable point of the cell (B)

The experiment performed revealed that there was a clear tendency both in the positive control Muscoril and in MILESAX to reduce the frequency of contractions per unit time and that the frequency of contractions was at least partly restored during washing (wash, exposure once again to differentiation medium, in the presence of carbacol, but in the absence of the treatments, FIG. 5A).

The mean displacement of the myotube during contraction is similar to the data noted in the literature (Manabe Y. et al., 2012, PLOS ONE 7(12): 1-10) and does not undergo variations during the treatments (FIG. 5B).

Figure 6:
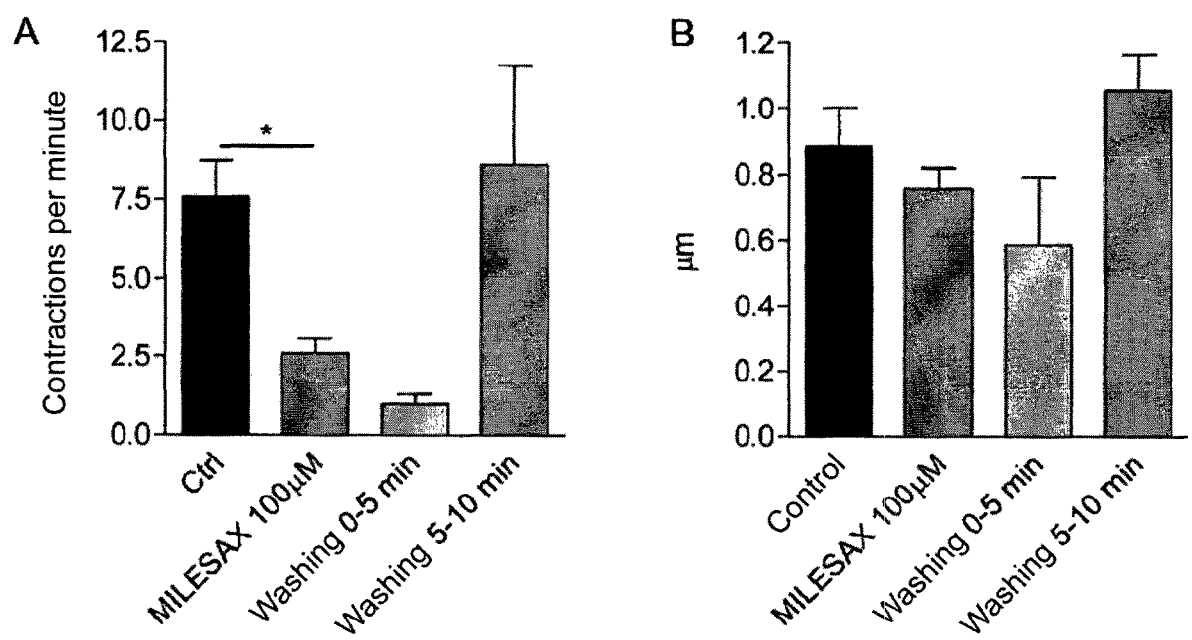
FIG. 6 shows the results of another experiment for quantifying the contractions per minute (A) and the average displacement of the myotube calculated as the distance traveled during a single contraction taken at an easily identifiable point of the cell (B).

The quantification of another experiment, in which the cell was exposed to MILESAX, is illustrated in FIG. 6. In this case, the effect of MILESAX on reducing the number of contractions per minute was statistically significant relative to the control. The myotube partly recovers the contraction frequency observed in the control after removal of MILESAX and exposure once again to differentiation medium.

The myotubes which did not at least partly recover contractile activity after exposure to the treatments and during washing were not considered.

Since the analysis of the contractile activity in the "live" experiments illustrated herein required long microscope acquisition times, to ensure the reliability of the reported data, it was not possible to compare the effects of MILESAX with the two positive controls suggested by the client, but only with one of the two (thiocolchicoside—Muscoril).

CONCLUSIONS

In conclusion, MILESAX demonstrated both anti-inflammatory properties in the THP-1 human monocyte cell model and muscle-relaxant properties in the human primary myotube cell model used for this study.

The invention claimed is:

1. A pharmaceutical composition or dietary supplement for muscle-relaxant and anti-inflammatory treatment, comprising active ingredients consisting of from 150 to 500 mg magnesium, from 100 to 300 mg L-tryptophan and from 100 to 300 mg Boswellia serrata dry extract as a source of ketoboswellic acid wherein the amounts are sufficient to achieve both muscle relaxant and anti-inflammatory effects and the pharmaceutical composition or dietary supplement is in an oral dosage form.

2. The pharmaceutical composition or dietary supplement according to claim 1, wherein said ketoboswellic acid is 3-acetyl- 11-keto-β-boswellic acid (AKBA).

3. The pharmaceutical composition or dietary supplement according to claim 1, wherein magnesium is in the form of magnesium bisglycinate.

4. The pharmaceutical composition or dietary supplement according to claim 1 comprising active agents consisting of about 225 mg of magnesium, about 175 mg of Boswellia serrata extract and about 150 mg of L-tryptophan.

5. The composition according to claim 1, further comprising pharmaceutically acceptable excipients and/or binders and/or vehicles.

* * * * *